United States Patent [19]

Lunn et al.

[11] Patent Number: 4,577,014
[45] Date of Patent: Mar. 18, 1986

[54] THIENO AND FUROPYRIDINIUM-SUBSTITUTED CEPHALOSPORINS

[75] Inventors: William H. W. Lunn; Robert T. Vasileff, both of Indianapolis, Ind.

[73] Assignee: Eli Lilly and Company, Indianapolis, Ind.

[21] Appl. No.: 679,514

[22] Filed: Dec. 7, 1984

Related U.S. Application Data

[60] Division of Ser. No. 449,945, Dec. 15, 1982, Pat. No. 4,501,739, which is a continuation-in-part of Ser. No. 340,628, Jan. 19, 1982, abandoned, which is a continuation-in-part of Ser. No. 300,357, Sep. 8, 1981, abandoned.

[51] Int. Cl.[4] ................. C07D 501/38; A61K 31/545
[52] U.S. Cl. ........................................ 544/22; 544/25; 544/27
[58] Field of Search ................. 544/22, 25, 27, 21

[56] References Cited

U.S. PATENT DOCUMENTS

| | | | |
|---|---|---|---|
| 4,258,041 | 3/1981 | O'Callaghan et al. | 424/246 |
| 4,267,176 | 5/1981 | Kamiyu et al. | 424/246 |
| 4,278,671 | 7/1981 | Ochiai et al. | 544/27 |
| 4,278,793 | 7/1981 | Durckheimer | 544/27 |
| 4,406,898 | 9/1983 | Lunn et al. | 544/27 |
| 4,430,499 | 2/1984 | Wheeler | 544/27 |
| 4,501,739 | 2/1985 | Lunn et al. | 544/22 |

FOREIGN PATENT DOCUMENTS 2098214 11/1982 United Kingdom .

*Primary Examiner*—Nicholas S. Rizzo
*Attorney, Agent, or Firm*—William B. Scanlon; Arthur R. Whale

[57] ABSTRACT

Cephalosporin compounds substituted in the 7-position by a 2-(5- or 6-membered heterocyclic)-2-oximinoacetylamino group and in the 3-position with a thienopyridinium methyl group or a furopyridinium methyl group are broad spectrum antibiotics highly effective in combating bacterial infections of gram-negative and gram-positive microorganisms. The cephalosporins are best prepared by reacting a silylated 7-[2-(heterocyclic)-2-oximinoacetylamino]-3-iodomethyl-3-cephem-4-carboxylic acid with the thienopyridine or the furopyridine. Pharmaceutical formulations comprising a compound of the invention and a method for treating bacterial infections comprising their use are also provided.

7 Claims, No Drawings

THIENO AND FUROPYRIDINIUM-SUBSTITUTED CEPHALOSPORINS

CROSS-REFERENCE TO RELATED APPLICATIONS

This application is a division of application Ser. No. 449,945, filed Dec. 15, 1982, now U.S. Pat. No. 4,501,739, as a continuation-in-part of application Ser. No. 340,628, filed Jan. 19, 1982, now abandoned, as a continuation-in-part of application Ser. No. 300,357, filed Sept. 8. 1981, now abandoned.

BACKGROUND OF THE INVENTION

This invention relates to cephalosporin antibiotics, to pharmaceutical formulations thereof, and to a method for treating bacterial infections. In particular, it relates to cephalosporin antibiotics which structurally possess a 7-[2-(amino-substituted 5- or 6-membered heterocyclic ring)-2-oximinoacetylamino] side chain and a bicyclic thieno- or furopyridinium group in the 3'-position of the cephalosporin bicyclic nucleus.

Prior to this invention, a number of cephalosporin antibiotics substituted in the 3'-position by a quaternary ammonium group and in the 7-position with various acylamino groups were known. Such compounds possess the betaine structure in that the positively-charged nitrogen atom of the quaternary ammonium group exists in the salt form with a anionic form of the $C_4$ carboxy group (carboxylate anion) of the cephalosporin. The well-known cephalosporin antibiotic cephaloridine, 7-(α-thienylacetamido)-3-(pyridinium-1-ylmethyl)-3-cephem-4-carboxylate, possesses the betaine structure.

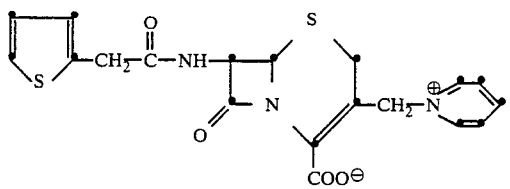

The first cephalosporin of this structural type was discovered by Hale, Newton, and Abraham, *Biochem. J.* 79, 403 (1961), upon the reaction of cephalosporin C with pyridine. Numerous other cephalosporin betaines with differing 7-acylamino side chains have been described since cephalosporin $C_A$ (pyridine) and cephaloridine were discovered.

Recently, Heymes et al., U.S. Pat. No. 4,152,432, described cephalosporin antibiotics having as the 7-acylamino side chain, a 7-[2-(2-aminothiazol-4-yl)-2-alkoxyiminoacetylamino] group and as the 3-position substituent an acetoxymethyl group. Others have prepared betaine derivatives of this antibiotic, e.g., as described in U.S. Pat. No. 4,098,888, by Takeda and in U.S. Pat. No. 4,258,041, by O'Callagan et al. Because the cephalosporin antibiotics possess potent antibacterial activity, intensive research in efforts to find improved broad spectrum cephalosporin antibiotics continues. In particular, these efforts seek improved cephalosporin antibiotics having potent broad spectrum activity coupled with activity against bacteria and bacterial strains known to be resistant to antibiotics in current use.

SUMMARY OF THE INVENTION

This invention provides semi-synthetic cephalosporin broad spectrum antibiotics. The antibiotics structurally possess, as the 7-position side chain, an amino-substituted 5- or 6-membered heterocyclic acetylamino group substituted in the α-position with an oximino group, and as the 3' substituent a thieno or furopyridinium group which may be substituted. For example, 7-[2-(2-aminothiazol-4-yl)-2-methoxyiminoacetamido]-3-(thieno[2,3-b]pyridinium-7-ylmethyl)-3-cephem-4-carboxylate and 7-[2-(2-aminothiazol-4-yl)-2-methoxyiminoacetamido]-3-(furo[3,2-c]pyridinium-5-ylmethyl)-3-cephem-4-carboxylate possess antibacterial activity against gram-positive and gram-negative bacteria.

The compounds are prepared for example by displacement of the halogen or acetoxy group of a 3-halomethyl or 3-acetoxymethyl substituted cephalosporin with a thienopyridine or a furopyridine.

DETAILED DESCRIPTION

The compounds provided by this invention are represented by the following formula 1

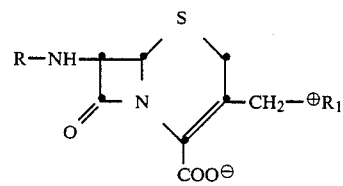

wherein R is hydrogen, formyl, α-aminoadipoyl, protected α-aminoadipoyl, or an acyl group represented by the formula

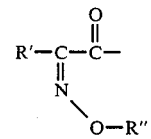

wherein R' is a 5- or 6-membered heterocyclic ring represented by the formulas

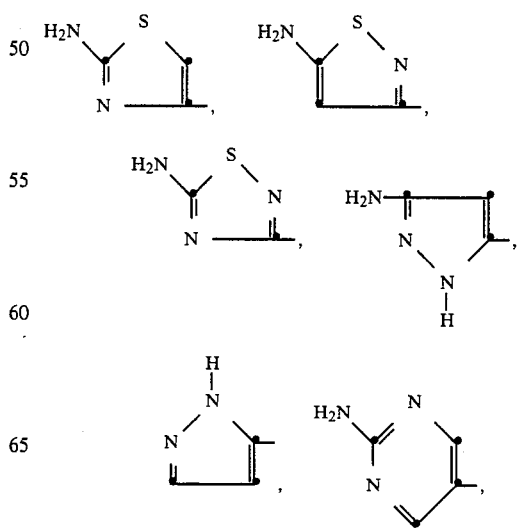

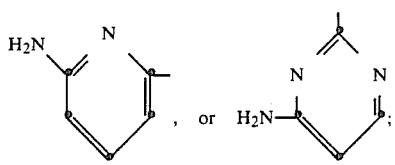

R″ is hydrogen, $C_1$–$C_4$ alkyl, a carboxy-substituted alkyl or carboxy-substituted cycloalkyl group represented by the formula

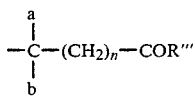

wherein n is 0–3, a and b when taken separately are independently hydrogen or $C_1$–$C_3$ alkyl, or when taken together with the carbon to which they are attached form a $C_3$–$C_7$ carbocyclic ring; R‴ is hydroxy, amino, $C_1$–$C_4$ alkoxy, or OR° wherein R° is indanyl, phthalidyl, an acyloxymethyl group of the formula —CH₂—OC(O)R₂, wherein R₂ is $C_1$–$C_4$ alkyl or phenyl; or R° is a carboxy-protecting ester group; or R″ is a carbamoyl group represented by the formula

wherein R″″ is $C_1$–$C_4$ alkyl, phenyl, or $C_1$–$C_3$ alkyl substituted by phenyl; ⊕R₁ is bicyclicpyridinium group selected from the group consisting of a thienopyridinium group represented by the formulas

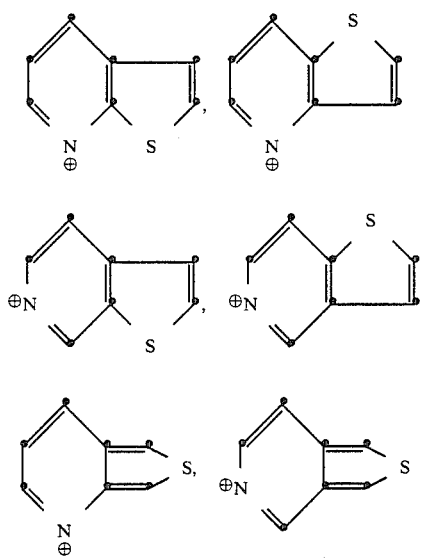

or a furopyridinium group represented by the formulas

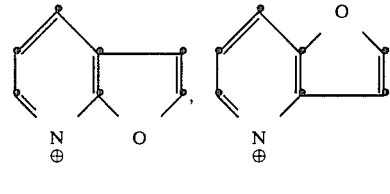

where in the above formulas either or both of the hetero rings can be substituted by one or two $C_1$–$C_4$ alkyl, halogen, trifluoromethyl, carboxy, carbamoyl, —SO₃H, hydroxy, $C_1$–$C_4$ alkoxy, amino, mono-($C_1$–$C_4$ alkyl)amino, di-($C_1$–$C_4$ alkyl)amino, $C_2$–$C_4$ alkanoylamino, aminosulfonyl, cyano, formyl, $C_1$–$C_4$ alkoxycarbonyl, or a hydroxyamide group of the formula

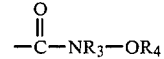

wherein R₃ and R₄ are independently hydrogen or $C_1$–$C_4$ alkyl; and when R is an acyl group, the pharmaceutically acceptable non-toxic salts thereof.

The terms used in the definition of the compounds of the formula 1 have the following meanings herein: "$C_1$–$C_4$ alkyl" refers to methyl, ethyl, n-propyl, isopropyl, n-butyl, t-butyl, sec-butyl, and the like; "$C_1$–$C_4$ alkoxy" refers to methoxy, ethoxy, n-propoxy, isopropoxy, n-butoxy, t-butoxy, sec-butoxy, and the like; "$C_1$–$C_3$ alkyl" refers to methyl, ethyl, n-propyl, and isopropyl; "$C_1$–$C_3$ alkyl substituted by phenyl" refers to benzyl, 2-phenethyl, 1-phenethyl, 3-phenylpropyl, 2-phenylpropyl, and the like; and "$C_3$–$C_7$ carbocyclic ring" refers to cyclopropyl, cyclobutyl, cyclopentyl, cyclohexyl, and cycloheptyl. "Halogen" refers to fluoro, chloro, or bromo. The term "hydroxyamide" refers to the N-hydroxyamide group (hydroxamic acid) and the N-alkyl-N-hydroxyamide, and N-alkoxyamide, and the N,O-dialkylamide groups such as N-hydroxycarbamoyl, N-methoxycarbamoyl, N-methyl-N-methoxycarbamoyl, N-methyl-N-hydroxycarbamoyl, N-ethyl-N-hydroxycarbamoyl, and like lower alkyl substituted hydroxyamido groups. "$C_2$–$C_4$ alkanoylamino" refers to acetamido, propionamido, butyramido, and like acylamino groups. The term "di-($C_1$–$C_4$ alkyl)amino" refers to dialkylamino and mixed dialkylamino groups such as dimethylamino, diethylamino, di-n-propylamino, di-n-butylamino, methylethylamino, methylbutylamino, ethyl-n-propylamino, and like groups.

The term "protected α-aminoadipoyl" refers to the α-aminoadipoyl acyl group in which the amino group and the carboxy group are blocked or protected with conventional protecting groups. For example, the amino group can be protected with an acyl or haloacyl group such as acetyl, chloroacetyl, propionyl, benzoyl, chlorobenzoyl, dichloro or dibromobenzoyl, phthaloyl, 2-carboxytetrachlorobenzoyl, 2-carboxytetrabromobenzoyl, and the like; or an alkyloxycarbonyl or aryloxycarbonyl group such as ethoxycarbonyl, trichloroethoxycarbonyl, t-butyloxycarbonyl, t-amyloxycarbonyl, benzyloxycarbonyl, or p-nitrobenzyloxycarbonyl, and like amino protecting groups. Conventional carboxy protecting groups are, for example, the ester forming groups commonly employed in the β-lactam antibiotic art to block or protect the acidic carboxy group during the preparation of antibiotic compounds. Examples of such groups are described hereinafter for the definition of the term R° of formula 1.

The carboxy-substituted alkyl and carboxy-substituted cycloalkyl groups represented by R" in formula 1 when R'" is hydroxy are exemplified by carboxymethyl, 2-carboxyethyl, 3-carboxypropyl, 4-carboxybutyl, 2-carboxyprop-2-yl, 2-carboxyprop-1-yl, 2-methyl-4-carboxybut-2-yl, 3-carboxy-3-methylprop-2-yl, 1-carboxycycloprop-1-yl, 1-carboxycyclobut-1-yl, 1-carboxycyclopent-1-yl, 1-carboxycyclohex-1-yl, 1-carboxymethylcyclobut-1-yl, 2-carboxyethylcyclohex-1-yl, and the like. When in the formula 1, R'" is $NH_2$, examples of the carboxamides represented are the amides of the above-named carboxy-substituted radicals.

The esters of the carboxy-substituted groups (formula 1, R" is carboxy-substituted alkyl or cycloalkyl and R'" is $C_1$–$C_4$ alkoxy) are illustrated by methoxycarbonylmethyl, ethoxycarbonylmethyl, 2-(ethoxycarbonyl)prop-2-yl, 1-propoxycarbonylcyclopent-1-yl, and like $C_1$–$C_4$ alkyl esters of the above-named carboxy-substituted alkyl and cycloalkyl radicals.

Examples of N-substituted carbamoyl groups (formula 1, R" is carbamoyl) are N-methylcarbamoyl, N-ethylcarbamoyl, N-propylcarbamoyl, N-phenylcarbamoyl, N-benzylcarbamoyl, and the like.

The terms "thienopyridinium" and "furopyridinium", represented by $\oplus R_1$ in the formula 1, refer to bicyclic thieno- and furopyridines which are bonded to the 3-position methylene group of the cephalosporin dihydrothiazine ring via the positively-charged nitrogen atom of the pyridine ring. As described herein, the compounds of the invention are betaines wherein the quaternary ammonium group exists with an anion, commonly, the $C_4$ carboxylate anion as depicted by the formula 1. The thienopyridines which can be used to form the compounds of the invention are represented by the following structural formulas wherein the numbering system indicated is employed herein in naming compounds of the invention.

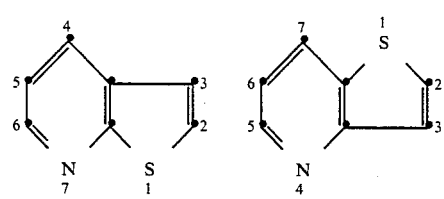

Thieno[2,3-b]pyridine    Thieno[3,2-b]pyridine

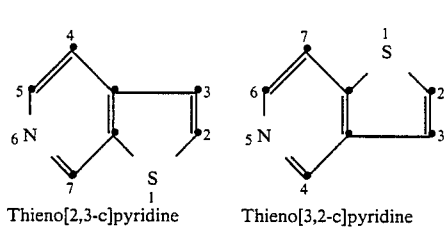

Thieno[2,3-c]pyridine    Thieno[3,2-c]pyridine

-continued

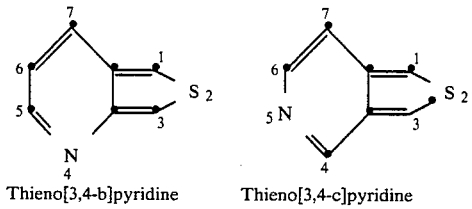

Thieno[3,4-b]pyridine    Thieno[3,4-c]pyridine

The thienopyridines are known compounds and are prepared as described in the art. Klemm, et al., *J. Org. Chem.*, 34, [2] 347–353 (1969) describe the preparation of thieno[2,3-b] and [3,2-b]pyridines; the thieno[3,4-b] and [3,4-c]pyridines are described by Klemm, et al., *J. Heterocyclic Chem.*, 9, 843 (1972); the thieno[2,3-c]pyridine is described by Klemm, et al., *J. Heterocyclic Chem.*, 5, 883 (1969), and the thieno[3,2-c]pyridine by S. Gronowitz and E. Sandberg, *Arkiv Kemi*, 32, 217 (1970), and Eloy, et al., *Bull. Soc. Chim. Belges*, 79, 301 (1970). The thieno[2,3-c] and [3,2-c]pyridines also are described by J. P. Maffrand and F. Eloy, *J. Heterocyclic Chem.*, 13, 1347 (1976).

The furopyridines used in the preparation of the compounds of the invention are known or can be prepared by known procedures. In the following formulas representing these furopyridines, the numbering system designated is used in naming the compounds of the invention.

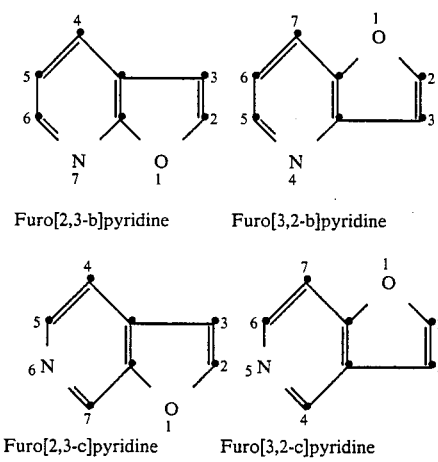

Furo[2,3-b]pyridine    Furo[3,2-b]pyridine

Furo[2,3-c]pyridine    Furo[3,2-c]pyridine

The furo[3,2-c]pyridines are prepared as described by F. Eloy, et al., *J. Het. Chem.* 8, 57–60, 1971. The furo[2,3-b]pyridines and the furo[3,2-b]pyridines are prepared by the methods described by J. W. McFarland, et al., *J. Heterocyclic Chem.*, 8, 735–738 (1971) and S. Gronowitz, et al., *Acta Chemica Scandinavica*, B-29, 233–238 (1975), respectively.

Furo[2,3-c]pyridine can be prepared by methods akin to those employed in the preparation of the corresponding thieno[2,3-c]pyridine by using either furfural or furan-3-aldehyde.

For example, furan-3-acrylic acid is converted to the acid azide by first reacting the acid with ethoxycarbonyl chloride and triethylamine to form the acid chloride and then reacting the mixed anhydride with sodium azide in water. The furan-3-acrylic acid azide is then heated in diphenylmethane with tributylamine to a temperature of about 190° C. to about 210° C. to form the furopyridone represented by the formula

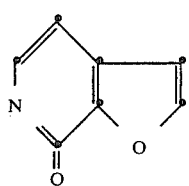

The furopyridone is allowed to react with phosphorus oxychloride to form 7-chlorofuro[2,3-c]pyridine and the latter is reductively dechlorinated with zinc in acetic acid to provide furo[2,3-c]pyridine.

Examples of substituted thienopyridines and substituted furopyridines are 2-methylfuro[2,3-b]pyridine, 6-ethylfuro[3,2-b]pyridine, 2-methylthieno[3,2-c]pyridine, 4-methyl-3-bromofuro[2,3-c]pyridine, 2-carboxythieno[3,2-c]pyridine, 2-carbamoylthieno[2,3-c]pyridine, 3-ethoxycarbonylfuro[3,2-c]pyridine, 5-methoxythieno[2,3-b]pyridine, 3-cyanofuro[3,2-b]pyridine, 3-aminothieno[3,2-b]pyridine, 3-acetamidothieno[3,2-b]pyridine, 2-sulfofuro[3,2-c]pyridine, 6-aminosulfonylthieno[3,2-b]pyridine, 6-hydroxyfuro[3,2-c]pyridine, 4-carboxythieno[2,3-c]pyridine, 2-(N-hydroxycarbamoyl)thieno[3,2-c]pyridine, 2-(N-methoxycarbamoyl)thieno[3,2-c]pyridine, 3-formylfuro[3,2-b]pyridine, and like groups.

The compounds of the invention wherein the bicyclicpyridinium group $\oplus R_1$ is substituted by a hydroxyamido group

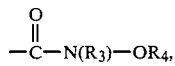

are obtained by reacting an ester of a carboxy-substituted bicyclicpyridine, eg. 2-methoxycarbonylthieno[3,2-c]pyridine, with hydroxylamine or an O-substituted hydroxylamine or an N,O-disubstituted hydroxylamine. The substituted bicyclicpyridine is then reacted with the desired silylated 3-iodomethyl cephalosporin to provide the desired compound. In the instance where $R_4$ of the hydroxyamido group is hydrogen, the acidic proton of the hydroxyamide is protected via silylation during the reaction with the silylated 3-iodomethyl cephalosporin.

Carboxy-protected derivatives of the compounds represented by the formula 1 when R'' is a carboxy-substituted alkyl or carboxy-substituted cycloalkyl group and R''' is OR°, are esters of the carboxy group commonly known in the art as carboxy-protecting or blocking groups. Examples of such ester groups (R°) are alkyl, alkenyl, and substituted alkyl ester groups such as t-butyl, 2-methylbutene-2-yl, 2,2,2-trichloroethyl, 2,2,2-tribromoethyl, and 2-iodoethyl; the benzyl ester and substituted benzyl esters such as p-methoxybenzyl and p-nitrobenzyl; the diphenylmethyl ester and substituted diphenylmethyl esters such as the 4-methoxydiphenylmethyl and 4,4'-dimethoxydiphenylmethyl esters; and trialkylsilyl esters such as trimethylsilyl; and like ester groups. The carboxy-protecting group is used for the temporary protection of the carboxy group as, for example, during the preparation of the compounds. These groups are readily removed under hydrolysis or hydrogenolytic conditions which are generally known in the art.

The esters represented by the formula 1 when R'' is a carboxy-substituted alkyl or a carboxy-substituted cycloalkyl group and R''' is OR°, namely the indanyl, phthalidyl, and acyloxymethyl esters, are biologically cleavable esters. Examples of such esters are the 5-indanyl, phthalidyl, acetoxymethyl, propionoxymethyl, pivaloyloxymethyl, and benzoyloxymethyl esters. The biologically cleavable esters are obtained by reacting the carboxylic acid function in the salt form, eg. the sodium or potassium salt, with bromophthalide, or with an acyloxymethyl halide, eg. acetoxymethyl bromide or pivaloyloxymethyl bromide. The indanyl ester is prepared with 5-indanol, the cephalosporin acid and a condensing agent.

The heterocyclic rings represented by R' in the formula 1 are named herein as follows: 2-aminothiazol-4-yl, 5-aminoisothiazol-3-yl, 5-amino-1,2,4-thiadiazol-3-yl, pyrazol-5-yl, 3-aminopyrazol-5-yl, 2-aminopyrimidin-5-yl, 4-aminopyrimidin-2-yl, and 2-aminopyridin-6-yl.

In the description of the compounds of the invention, the term "oximino" is used for convenience in describing the oxime and substituted oxime function

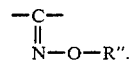

The compounds of the invention wherein R is an acyl group of the formula

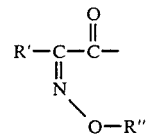

are broad spectrum antibiotics which inhibit the growth of microorganisms pathogenic to man and animals. For example, these compounds are effective in controlling the growth of the staphylococci and streptococci and penicillin-resistant strains of staphylococci. They also inhibit the growth of the gram-negative bacteria for example, proteus, pseudomonas, enterobacter, *Escherichia coli*, klebsiella, shigella, serratia, and salmonella.

The compounds represented by the formula 1 wherein R is hydrogen, formyl, aminoadipoyl, or protected aminoadipoyl are intermediates useful in the preparation of the compounds wherein R is an acyl group as described hereinafter.

The compounds of the invention wherein R is an acyl group as defined for formula 1 are prepared by the reaction of a thienopyridine or a furopyridine with a 7-acylaminocephalosporin represented by the formula 2

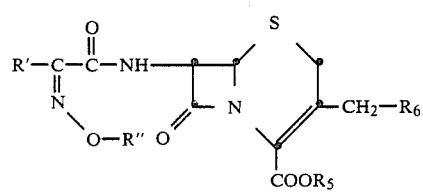

wherein R' and R'' have the same meanings as defined hereinabove, $R_5$ is hydrogen or a carboxy-protecting group, and $R_6$ is chloro, bromo, iodo, or acetoxy. The displacement reaction is preferably carried out with a compound of the formula 2 wherein $R_6$ is iodo. In the preferred method, a compound of the formula 2 wherein $R_6$ is iodo is first prepared by the reaction of a compound of the formula 2 wherein $R_6$ is acetoxy and $R_5$ is an ester group with trimethylsilyliodide (trimethyliodosilane) by the method of Bonjouklian, U.S. Pat. No. 4,266,049 issued May 5, 1981. The 3-iodomethyl cephalosporin is then reacted with the thienopyridine or furopyridine to provide a compound of the invention.

In carrying out the preferred process, a compound of the formula 2 ($R_6$ is acetoxy) is first silylated to form the silyl ester of the $C_4$ carboxy group and with other silyl reactive groups. The silylation is carried out at room temperature in an aprotic organic solvent with a silylating reagent such as mono- or bis-trimethylsilylacetamide, mono-trimethylsilyltrifluoroacetamide, or N-methyl-N-trimethylsilyltrifluoroacetamide. The silylated derivative is then reacted at ambient temperature with trimethylsilyliodide to provide the silylated 3-iodomethyl cephalosporin. The silylated 3-iodomethyl cephalosporin is then reacted with the thienopyridine or the furopyridine to provide a silylated compound of the invention. Hydrolysis of the silyl groups provides a compound of the invention.

The process is illustrated by the following reaction scheme wherein a trimethyl silylating reagent and a thieno[2,3-b]pyridine are exemplified.

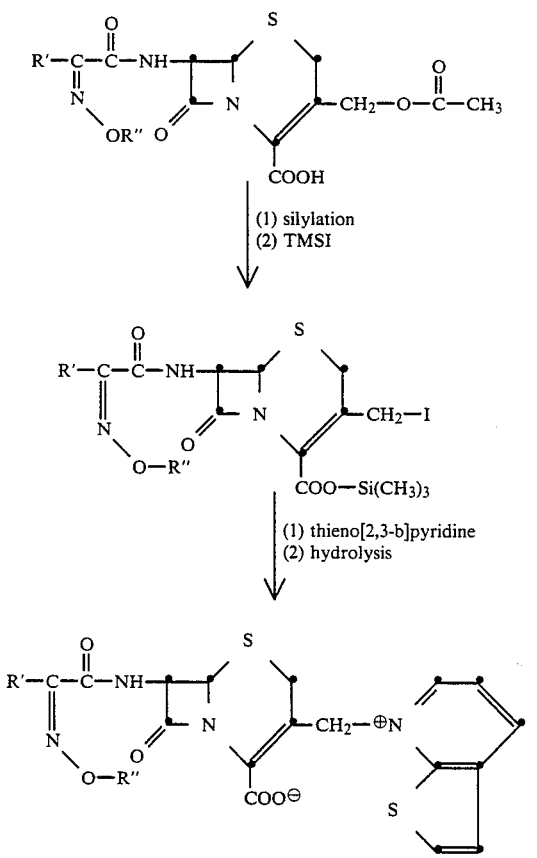

In the above scheme, R' and R" have the same meanings as defined hereinabove.

Alternatively, the antibiotic compounds of the invention can be prepared with a compound of the formula 2 ($R_6$ is acetoxy, $R_5$ is H) by displacement of the acetoxy group with the thienopyridine or furopyridine. The preparation is carried out in a known manner, for instance, in an aqueous medium, for example in a water miscible organic solvent containing water. The addition of a small amount of an alkali metal iodide such as potassium iodide can enhance the rate of the reaction. The reaction is carried out at a temperature between about 35° C. and about 70° C. Water miscible organic solvents such as acetone, acetonitrile, tetrahydrofuran, and dimethylacetamide are useful solvents.

This invention also provides the compounds represented by the formula 1 in the form of salts formed with strong acids and the salt form of biologically labile esters. Such salts are represented by the following formula 3

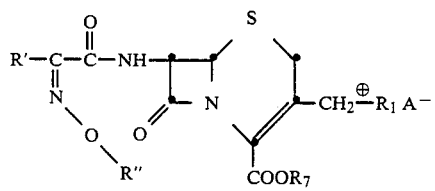

wherein R', R", and $R_1$ have the same meanings as defined for formula 1 and $R_7$ is hydrogen, indanyl, phthalidyl, or an acyloxymethyl group represented by the formula

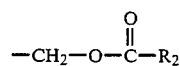

wherein $R_2$ has the same meanings as defined hereinabove; and $A^-$ is a chloride, bromide, iodide, sulfate, or phosphate anion.

Examples of acyloxymethyl ester groups, $R_7$, are acetoxymethyl, propionoxymethyl, pivaloyloxymethyl, and benzoyloxymethyl groups.

A compound of the formula 1 is converted to its strong acid salt with acids such as hydrochloric acid, hydrobromic acid, sulfuric acid, or phosphoric acid.

The biologically labile esters are prepared with a compound of the formula 1 and an acyloxymethyl halide, an indanyl halide eg. 5-bromoindane or phthalidyl bromide. Upon esterification the salt form of the ester is obtained. For example, with acetoxymethyl bromide the acetoxymethyl ester bromide is obtained (formula 3, $R_2$ is acetoxymethyl, $A^-$ is $Br^-$).

It will be appreciated that when in a compound represented by the formula 1 R" is a carboxy-substituted alkyl or cycloalkyl group and R''' is hydroxy, the di-biologically labile esters may be prepared. Likewise it will be appreciated that acid addition salts will be formed with any basic amino groups present in the molecule (i.e. formula 1) wherein an amino-substituted heterocyclic group is present) when the strong acid salts represented by formula 3 are prepared.

The biologically labile ester salts and the strong acid salts represented by the formula 3 are alternative forms of the compounds represented by the formula 1 and may be formulated for administration in therapy.

The compounds of the formula 1, wherein R is hydrogen or formyl, are prepared with 7-aminocephalosporanic acid and 7-formamidocephalosporanic acid, respectively, by displacement of the 3'-acetoxy group with the thienopyridine or furopyridine as described above. Alternatively, 7-formamido-3-iodomethyl-3-cephem-4-carboxylic acid trimethylsilyl ester is prepared by the Bonjouklian method as described above and is then reacted with the thienopyridine or the furopyridine to provide the compound of the formula 1 wherein R is formyl.

Alternatively, the 7-amino nucleus compounds of the formula 1 (R is H) are prepared by the well-known N-deacylation reaction which proceeds through an imino chloride to an imino ether and thence on decomposition of the latter to the 7-amino-3-bicyclicpyridinium-4-carboxylate. Initially, a 7-acylaminocephalosporanic acid, wherein the 7-acyl group can be for example phenylacetyl, phenoxyacetyl or a heterocyclic acyl group such as thienylacetyl, is reacted with the bicyclicpyridine to form the 7-acylamino-3-bicyclicpyridinium-methyl)-3-cephem-4-carboxylate. Alternatively, the latter compound is obtained via the 7-acylamino-3-iodomethyl ester (Bonjouklian method) which is allowed to react with the bicyclicpyridine. The 7-acyl bicyclopyridinium compound is then treated with an imino halide-forming reagent such as phosphorus pentachloride in an inert solvent in the presence of an acid-binding agent such as a tertiary amine e.g., diethylaniline to provide the imino halide derivative of the 7-position acylamido group. Without isolation, the imino halide is treated with an alcohol, alkanediol or benzyl alcohol to form the corresponding imino ether. Decomposition of the imino ether provides the 7-amino nucleus compound.

In an example of the preparation of a 7-amino nucleus compound by this method, 7-(2-thienylacetamido)cephalosporanic acid is reacted with thieno[2,3-b]pyridine to prepare 7-(2-thienylacetamido)-3-(thieno[2,3-b]pyridinium-7-ylmethyl)-3-cephem-4-carboxylate. The latter is converted to the trimethylsilyl ester with trimethylchlorosilane in a halogenated hydrocarbon solvent in the presence of dimethylacetamide (weak base) in an amount corresponding to a 4–5 molar excess. Solvents such as methylene chloride, trichloroethane, and chloroform are suitable. The solution of the silyl ester is cooled to a temperature of about $-30°$ C. to about $0°$ C. and an imino halide-forming reagent such as phosphorus pentachloride is added. After imino halide formation is complete, a $C_1-C_4$ alkanol, an alkanediol, or a benzyl alcohol is added to the cold reaction mixture. The temperature of the reaction mixture is allowed to warm to about room temperature and the product, 7-amino-3-(thieno[2,3-b]pyridinium-7-ylmethyl)-3-cephem-4-carboxylic acid, precipitates in the form of the dihydrochloride salt represented by the formula

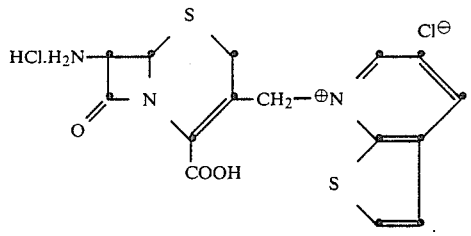

The N-formyl compounds (formula 1, R is formyl) are useful as intermediates in the preparation of the antibiotic compounds of the invention. For example, 7-formamidocephalosporanic acid is silylated and the silyl ester converted to the 3-iodomethyl derivative with trimethylsilyliodide as described hereinabove. The 3-iodomethyl silylated derivative is reacted with the bicyclicpyridine to form the compound represented by the formula 1. The N-formyl-3-thienopyridinium-methyl-3-cephem is then converted to the 7-amino nucleus compound with methanolic hydrochloric acid.

The 7-amino-3-(bicyclicpyridinium-methyl)-3-cephem-4-carboxylate or the dihydrochloride salt thereof is also obtained with cephalosporin C wherein the amino and carboxy groups are protected. For example, cephalosporin C is first silylated with a conventional silylating reagent such as N-methyl-N-trimethylsilyltrifluoroacetamide to form the N-trimethylsilyl ditrimethylsilyl ester derivative. The latter is reacted with TMSI by the Bonjouklian method, and the 3-iodomethyl silylated derivative of cephalosporin C which is obtained is then allowed to react with the thienopyridine or the furopyridine and, following hydrolysis of the silyl groups, the compound of the formula 1 wherein R is α-aminoadipoyl is obtained. The α-aminoadipoyl side chain is cleaved by the N-deacylation procedure described above. In carrying out the N-deacylation, the amino group and the carboxy groups of the molecule are protected.

In carrying out the preparation of a 7-amino-3-(bicyclicpyridinium-methyl)-3-cephem-4-carboxylate with cephalosporin C, use can be made of the silylated 3-(bicyclicpyridinium-methyl) derivative obtained in the Bonjouklian method as described above. Since the amino group and the two carboxy groups are silylated, and thus protected, the N-deacylation can be carried out directly on this protected intermediate. During the final step of the N-deacylation, i.e. following the formation of the imino ether of the side chain moiety, water is added to effect the hydrolysis of the silyl protecting group. The above-described preparation is illustrated by the following reaction scheme.

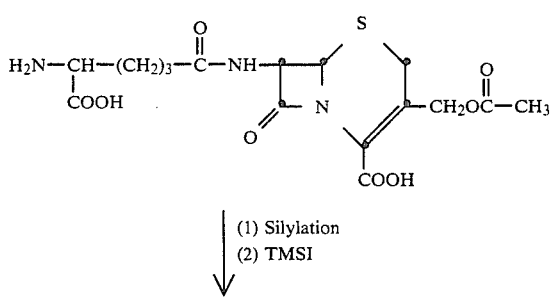

-continued

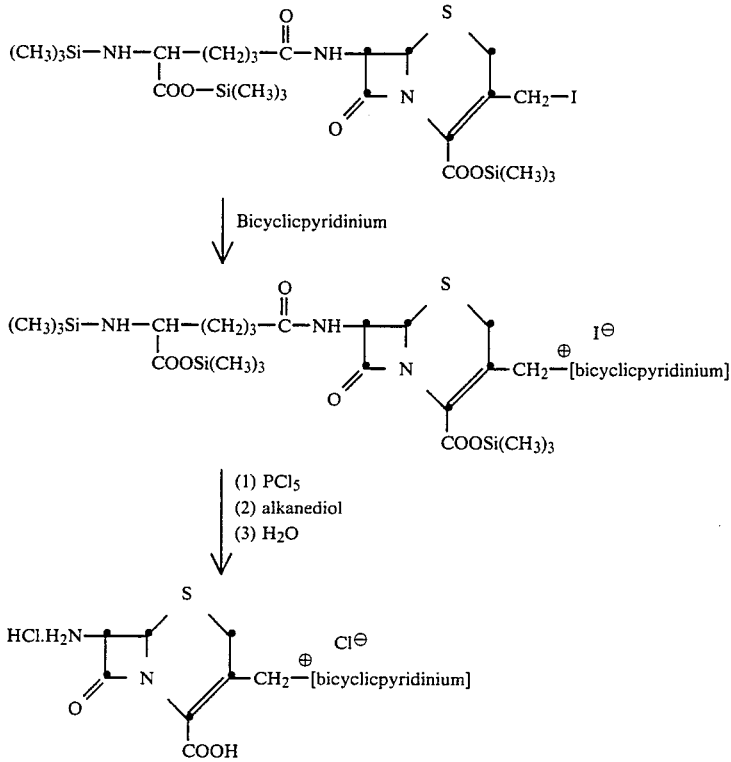

Alternatively, the 7-amino-3-(bicyclicpyridinium-methyl) nucleus compound can be obtained with cephalosporin C having the amino group and the carboxy groups protected. Examples of such protecting groups which can be used are given hereinabove for the definition of the term "protected aminoadipoyl".

The 7-amino nucleus compound (formula 1, R=H) prepared by the N-deacylation method or via the N-formyl derivative is acylated with an active carboxy derivative of a 2-(heterocyclic)-2-oximinoacetic acid represented by the formula

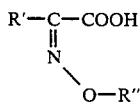

to provide an antibiotic compound of the formula 1. The N-acylation coupling reaction is carried out by acylation methods well-known in the art. Active derivatives of the carboxy group such as the so-called "active esters" can be used. Examples of active esters are those formed with the oximino acetic acid and hydroxybenzotriazole (HBT), or hydroxysuccinimide; and the esters formed with methyl chloroformate and isobutyl chloroformate. The acylation can also be carried out by employing the acid halide, e.g. the acid chloride, in the presence of an acid scavenger such as sodium bicarbonate or triethylamine.

The amino group of the amino-substituted heterocycles (R' in formula 1) is desirably protected during the N-acylation of the 7-amino nucleus compound. Amino-protecting groups which can be used are those commonly employed in the cephalosporin art for the temporary protection of basic amino groups to block or prevent their interference in a reaction carried out at another site in the molecule. Examples of such groups are the haloacyl groups such as chloroacetyl and dichloroacetyl; the urethane-forming protecting groups such as t-butyloxycarbonyl, 2,2,2-trichloroethoxycarbonyl, cyclopentyloxycarbonyl, adamantyloxycarbonyl, benzyloxycarbonyl, p-nitrobenzyloxycarbonyl, and diphenylmethyloxycarbonyl; and other protecting groups such as trityl (triphenylmethyl) and benzhydryl.

The compounds represented by the formula 2 wherein $R_6$ is an acetoxy group are prepared by known methods. For example, compounds wherein R' is the 2-aminothiazol-4-yl group are described by Heymes et al., U.S. Pat. No. 4,152,432; compounds wherein R' is 2-aminopyridin-6-yl, 2-aminopyrimidin-5-yl, or 4-aminopyrimidin-2-yl, are described by U.S. Pat. No. 4,167,176; compounds wherein R' is 5-amino-1,2,4-thiadiazol-3-yl are described by EPO Application No. 0,007,470; compounds wherein R" is an N-substituted carbamoyl group are prepared by the methods described by U.S. Pat. No. 4,200,575; and compounds wherein R' is 3-aminopyrazol-5-yl, or pyrazol-5-yl are obtained as described by U.K. Patent Application No. 2,046,734A.

Commonly, the compounds of the formula 2 wherein $R_6$ is acetoxy are prepared by the N-acylation of the 7-amino group of 7-aminocephalosporanic acid, or an ester thereof, with the 2-(heterocyclic)-2-oximinoacetic acid by employing acylation methods known in the art. For example, the heterocyclic oximino-substituted acetic acid is converted to an active ester such as the ester formed with hydroxybenzotriazole or hydroxysuccinimide, and the active ester is used as the acylating moiety. Other active derivatives of the carboxylic acid such as the acid chloride or acid azide can be used in the acylation.

The compounds of the formula 2 wherein R' is a pyrazol-5-yl or 3-aminopyrazol-5-yl group are prepared by employing methods known in the art. The 2-(pyrazol-5-yl)-2-oximinoacetic acid or the 2-(3-aminopyrazol-5-yl)-2-oximinoacetic acid is prepared and converted to an active derivative of the carboxylic acid, for example, an active ester. The active ester is coupled, via N-acylation, with 7-aminocephalosporanic acid and the 7-[2-(pyrazol-5-yl)-2-oximinoacetamido]-3-acetoxymethyl-3-cephem-4-carboxylic acid and 7-[2-(3-aminopyrazol-5-yl)-2-oximinoacetamido]-3-acetoxymethyl-3-cephem-4-carboxylic acid are converted to the corresponding 3-idomethyl silylated derivatives as described herein. The latter are reacted with the thienopyridine to provide the respective compound of the invention.

The pyrazole and aminopyrazole oximino substituted acetic acids are prepared by employing synthetic methods known in the art. For example, the 2-(pyrazol-5-yl)-2-alkoxyiminoacetic acid is prepared by heating in an inert hydrocarbon solvent the acetyl oximino compound of the formula A

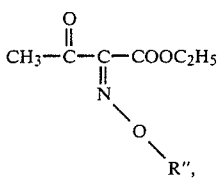

wherein R" is other than hydrogen as defined above, with dimethylformamide dimethylacetal to form the dimethylaminomethylene oximino ester of the formula

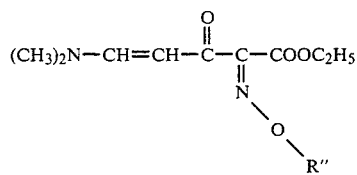

The latter is reacted with hydrazine hydrate to provide the ethyl ester of 2-(pyrazol-5-yl)-2-alkoxyiminoacetic acid. The ester is hydrolyzed to the free acid and the acid converted to an active ester for acylation.

The 2-(3-aminopyrazol-5-yl)-2-alkoxyiminoacetic acid is prepared by reacting the compound of the formula A with carbon disulfide and two equivalents of methyl iodide to form the intermediate compound of the formula B

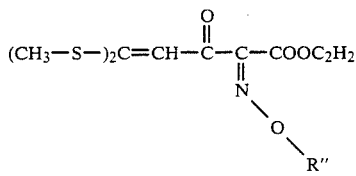

Intermediate B is reacted with N-t-BOC hydrazine to provide compound C,

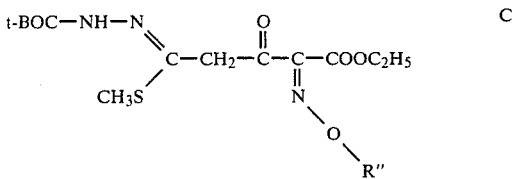

and C is reacted with hydrazine hydrate to form 2-(3-t-BOC-hydrazinopyrazol-5-yl)-2-oximinoacetic acid ethyl ester D.

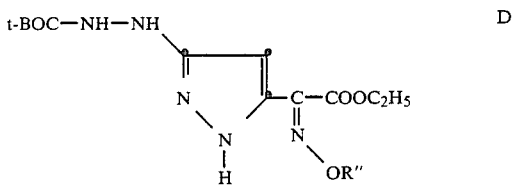

Compound D is treated in the cold with trifluoroacetic acid to remove the t-BOC group and the 3-hydrazinopyrazole is nitrosated with nitrous ($HNO_2$) acid in the cold to form 2-(3-azidopyrazol-5-yl)-2-oximinoacetic acid ethyl ester. The azido group is reduced to the amino group by chemical reduction to provide the 2-(3-aminopyrazol-5-yl)-oximinoacetic acid ethyl ester. The ester is hydrolyzed under alkaline conditions to the free acid.

The compounds of the invention have the same stereochemistry as the known cephalosporin antibiotics. The 7-position side chain has the natural β-configuration (6R, 7R), while the oximino group in the side chain can exist in either the syn or anti forms or as a mixture of both. Compounds of the invention in either form are prepared by employing the 2-(heterocyclic)-2-oximinoacetic acid acylating moiety in the syn or anti form. Alternatively, mixtures of the syn and anti compounds of the formula 1 can be separated by chromatographic means such as by HPLC. The compounds in the syn form are preferred because of their higher activity.

Examples of bicyclicpyridinium compounds of the invention represented by the formula 1 wherein R is an acyl group include the following compounds:

7-[2-(2-aminothiazol-4-yl)-2-hydroxyiminoacetamido]-3-(thieno[2,3-b]pyridinium-7-ylmethyl)-3-cephem-4-carboxylate, 7-[2-(2-aminothiazole-4-yl)-2-methoxyiminoacetamido]-3-(thieno[2,3-b]pyridinium-7-ylmethyl)-3-cephem-4-carboxylate, 7-[2-(2-aminothiazole-4-yl)-2-ethoxycarbonylmethoxyiminoacetamido]-3-(thieno[2,3-b]pyridinium-7-ylmethyl)-3-cephem-4-carboxylate, 7-[2-(2-aminothiazole-4-yl)-2-methoxyiminoacetamido]-3-(thieno[3,2-b]pyridinium-4-ylmethyl)-3-cephem-4-carboxylate, 7-[2-(2-aminothiazol-4-yl)-2-methoxyiminoacetamido]-3-(thieno[2,3-c]pyridinium-6-ylmethyl)-3-cephem-4-carboxylate, 7-[2-(2-aminothiazol-4-yl)-2-methoxyiminoacetamido]-3-(thieno[3,2-c]pyridinium-5-ylmethyl)-3-cephem-4-carboxylate, 7-[2-(2-aminothiazol-4-yl)-2-methoxyiminoacetamido]-3-(thieno[3,4-b]pyridinium-4-ylmethyl)-3-cephem-4-carboxylate, 7-[2-(2-aminothiazol-4-yl)-2-methoxyiminoacetamido]-3-(thieno[3,4-c]pyridinium-5-ylmethyl)-3-cephem-4-carboxylate, 7-[2-(2-aminopyridin-6-yl)-2-(2-carboxypropyl)oxyiminoacetamido]-3-(thieno[3,4-b]pyridinium-4-ylmethyl)-3-cephem-4-carboxylate, 7-[2-(5-amino-1,2,4-thiadiazol-3-yl)-2-methoxyiminoacetamido]-3-(thieno[2,3-b]pyridinium-7-ylmethyl)-3-cephem-4-carboxylate, 7-[2-(5-aminoisothiazol-3-yl)-2-(2-carboxyprop-2-yl)oxyiminoacetamido]-3-(thieno[2,3-c]pyridinium-6-ylmethyl)-3-cephem-4-carboxylate, 7-[2-(2-aminopyrimidin-5-yl)-2-ethoxyiminoacetamido]-3-(thieno[3,2-b]pyridinium-4-ylmethyl)-3-cephem-4-carboxylate, 7-[2-(4-aminopyrimidin-2-yl)-2-(N-methylcarbamoyloxy)iminoacetamido]-3-(thieno[3,2-c]pyridinium-5-ylmethyl)-3-cephem-4-carboxylate, 7-[2-(2-aminopyridin-6-yl)-2-methoxyiminoacetamido]-3-(thieno[3,2-b]pyridinium-4-ylmethyl)-3-cephem-4-carboxylate, 7-[2-(3-aminopyrazol-5-yl)-2-methoxyiminoacetamido]-3-(thieno[2,3-b]pyridinium-7-ylmethyl)-3-cephem-4-carboxylate, 7-[2-(3-aminopyrazol-5-yl)-2-ethoxycarbonylmethoxyiminoacetamido]-3-(thieno[3,2-c]pyridinium-5-ylmethyl)-3-cephem-4-carboxylate, 7-[2-(pyrazol-5-yl)-2-methoxycarbonylmethoxyiminoacetamido]-3-(thieno[3,2-b]pyridinium-4-ylmethyl)-3-cephem-4-carboxylate, 7-[2-(pyrazol-5-yl)-2-ethoxycarbonylmethoxyiminoacetamido]-3-(thieno[2,3-c]pyridinium-6-ylmethyl)-3-cephem-4-carboxylate, 7-[2-(pyrazol-5-yl)-2-methoxyiminoacetamido]-3-(thieno[3,2-b]pyridinium-4-ylmethyl)-3-cephem-4-carboxylate, 7-[2-(2-aminothiazol-4-yl)-2-(2-carboxyprop-2-yl)oxyiminoacetamido]-3-(thieno[3,2-c]pyridinium-5-ylmethyl)-3-cephem-4-carboxylate, 7-[2-(2-aminothiazol-4-yl)-2-(2-carboxyprop-2-yl)oxyiminoacetamido]-3-(thieno[3,2-b]pyridinium-4-ylmethyl)-3-cephem-4-carboxylate, 7-[2-(2-aminothiazol-4-yl)-2-(2-carboxyprop-2-yl)oxyiminoacetamido]-3-(thieno[2,3-c]pyridinium-6-ylmethyl)-3-cephem-4-carboxylate, 7-[2-(2-aminothiazol-4-yl)-2-(2-carboxyprop-2-yl)oxyiminoacetamido]-3-(thieno[3,4-b]pyridinium-7-ylmethyl)-3-cephem-4-carboxylate, 7-[2-(2-aminopyridin-6-yl)-2-methoxyiminoacetamido]-3-(thieno[2,3-c]pyridinium-6-ylmethyl)-3-cephem-4-carboxylate, 7-[2-(2-aminopyridin-6-yl)-2-methoxyiminoacetamido]-3-(thieno[3,2-c]pyridinium-5-ylmethyl)-3-cephem-4-carboxylate, 7-[2-(2-aminopyridin-6-yl)-2-ethoxycarbonylmethoxyiminoacetamido]-3-(thieno[2,3-c]pyridinium-6-ylmethyl)-3-cephem-4-carboxylate, 7-[2-(5-amino-1,2,4-thiadiazol-3-yl)-2-oximinoacetamido]-3-(thieno[2,3-b]pyridinium-7-ylmethyl)-3-cephem-4-carboxylate, 7-[2-(2-aminothiazol-4-yl)-2-methoxyiminoacetamido]-3-(4-methylthieno[2,3-b]pyridinium-7-ylmethyl)-3-cephem-4-carboxylate, 7-[2-(2-aminothiazol-4-yl)-2-methoxyiminoacetamido]-3-(7-methylthieno[3,2-b]pyridinium-4-ylmethyl)-3-cephem-4-carboxylate, 7-[2-(2-aminothiazol-4-yl)-2-methoxyiminoacetamido]-3-(2-ethylthieno[2,3-b]pyridinium-7-ylmethyl)-3-cephem-4-carboxylate, 7-[2-(2-aminothiazol-4-yl)-2-ethoxyiminoacetamido]-3-(2,3-dibromothieno[2,3-b]pyridinium-7-ylmethyl)-3-cephem-4-carboxylate, 7-[2-(pyrazol-5-yl)-2-ethoxycarbonylmethoxyiminoacetamido]-3-(7-methylthieno[3,2-c]pyridinium-4-ylmethyl)-3-cephem-4-carboxylate, 7-[2-(2-aminothiazol-4-yl)-2-methoxyiminoacetamido]-3-(furo[2,3-c]pyridinium-6-ylmethyl)-3-cephem-4-carboxylate, 7-[2-(2-aminothiazol-4-yl)-2-methoxyiminoacetamido]-3-(furo[3,2-c]pyridinium-5-ylmethyl)-3-cephem-4-carboxylate, 7-[2-(2-aminothiazol-4-yl)-2-methoxyiminoacetamido]-3-(furo[2,3-b]pyridinium-7-ylmethyl)-3-cephem-4-carboxylate, 7-[2-(2-aminothiazol-4-yl)-2-methoxyiminoacetamido]-3-(2-methylfuro[3,2-c]pyridinium-5-ylmethyl)-3-cephem-4-carboxylate, 7-[2-(2-aminothiazol-4-yl)-2-methoxyiminoacetamido]-3-(2,7-dimethylfuro[3,2-c]pyridinium-5-ylmethyl)-3-cephem-4-carboxylate, 7-[2-(2-aminothiazol-4-yl)-2-(2-carboxyprop-2-yl)oxyiminoacetamido]-3-(furo[3,2-c]pyridinium-5-ylmethyl)-3-cephem-4-carboxylate, 7-[2-(5-amino-1,2,4-thiadiazol-3-yl)-2-methoxyiminoacetamido]-3-(furo[3,2-c]pyridinium-5-ylmethyl)-3-cephem-4-carboxylate, 7-[2-(pyrazol-5-yl)-2-ethoxycarbonylmethoxyiminoacetamido]-3-(furo[3,2-c]pyridinium-5-ylmethyl)-3-cephem-4-carboxylate, 7-[2-(2-aminothiazol-4-yl)-2-methoxyiminoacetamido]-3-(furo[3,2-b]pyridinium-4-ylmethyl)-3-cephem-4-carboxylate, 7-[2-(2-aminothiazol-4-yl)-2-(2-carboxyprop-2-yl)oxyiminoacetamido]-3-(furo[3,2-b]pyridinium-4-ylmethyl)-3-cephem-4-carboxylate, 7-[2-(2-aminopyrimidin-5-yl)-2-ethoxyiminoacetamido]-3-(2-methylfuro[3,2-b]pyridinium-4-yl-methyl)-3-cephem-4-carboxylate, 7-[2-(2-aminothiazol-4-yl)-2-hydroxyiminoacetamido]-3-(furo[3,2-c]pyridinium-5-ylmethyl)-3-cephem-4-carboxylate, 7-[2-(3-aminopyrazol-5-yl)-2-methoxyiminoacetamido]-3-(furo[2,3-b]pyridinium-7-ylmethyl)-3-cephem-4-carboxylate, 7-[2-(2-aminothiazol-4-yl)-2-(2-carboxyprop-2-yl)oxyiminoacetamido]-3-(2,4-dimethylfuro[2,3-b]pyridinium-7-ylmethyl)-3-cephem-4-carboxylate, and 7-[2-(5-amino-1,2,4-thiadiazol-3-yl)-2-methoxyiminoacetamido]-3-(furo[2,3-b]pyridinium-7-ylmethyl)-3-cephem-4-carboxylate.

A preferred group of compounds of the invention is represented by the formula 1 wherein $\oplus R_1$ is a 2,3-b, 3,2-b, 2,3-c, or 3,2-c thienopyridine. Preferred compounds of the invention are also represented by the formula 1 wherein R is an acyl group and R' is 2-aminothiazol-4-yl and R" is $C_1$–$C_4$ alkyl, preferably methyl, or a carboxy-substituted alkyl group, preferably 2-carboxyprop-2-yl, 2-carboxymethyl, or 2-carboxyethyl.

Another preferred group of compounds are represented by the formula 1 wherein $\oplus R_1$ is a furopyridinium group, especially a furo[3,2-c], furo[3,2-b] or furo[2,3-c]pyridinium group.

Especially preferred compounds of the invention are represented by the formula 1 wherein R' is 2-aminothiazol-4-yl, R" is methyl or 2-carboxyprop-2-yl, and ⊕R₁ is a thieno or furopyridinium group substituted in the thieno of furo ring by methyl or carboxy. Preferably, the compounds are carboxy substituted. Such substituted compounds of the invention are potent antibacterials having decreased or minimal undesirable side effects. Three such preferred compounds are syn-7-[2-(2-aminothiazol-4-yl)-2-methoxyiminoacetamido]-3-(2-carboxyfuro[3,2-b]pyridinium-4-ylmethyl)-3-cephem-4-carboxylate, syn-7-[2-(2-aminothiazol-4-yl)-2-methoxyiminoacetamido]-3-(2-carboxythieno[3,2-c]pyridinium-5-ylmethyl)-3-cephem-4-carboxylate and the corresponding 3-carboxythieno[3,2-c]pyridinium substituted cephalosporin.

The compounds of the invention, both the thienopyridinium and furopyridinium-substituted compounds, exhibit little if any nephrotoxicity in in vitro tests.

The antibiotic compounds of the invention and the pharmaceutically acceptable salts thereof (formula 1, R is acyl) can be formulated into pharmaceutical compositions useful in the treatment of infectious diseases. Accordingly, this invention provides pharmaceutical compositions comprising as the active ingredient an antibiotic compound of the invention or a pharmaceutically acceptable non-toxic salt thereof and a pharmaceutical diluent. Compositions for parenteral administration of the antibiotics or a salt thereof comprise the antibiotic or salt at a suitable concentration in a diluent such as Water-For-Injection, 5% dextrose, 0.9% saline, 5% glucose, or other pharmaceutically acceptable diluent. Such compositions are commonly prepared just prior to use as, for example, prior to intramuscular injection or intravenous infusion. An example of a composition of the invention useful for intramuscular administration comprises 0.5 g. of an antibiotic of the invention in 3 ml. of Water-For-Injection.

An example of a composition for intravenous use comprises between about 500 mg. to about 1 g. of an antibiotic of the invention in between about 50 ml. and 100 ml. of 0.9% saline. The intravenous solution can be prepared, for example, with a unit dosage formulation of the antibiotic in a plastic bag, by adding the diluent to the bag prior to infusion.

The compounds of the invention may be administered intrarectally for example in a suitably formulated suppository. Pharmaceutically acceptable suppository formulations can be prepared with the antibiotic compound and a suppository composition such as cocoa butter, hydrogenated fats, glycerides, or polyethylene glycols.

Pharmaceutical compositions of the invention also include unit dosage formulations. Such formulations comprise between about 200 mg. and about 10 g. of the antibiotic or a pharmaceutically acceptable non-toxic salt thereof in solid form in a sterile ampoule, vial or a plastic container such as a bag adapted for i.v. administration. The antibiotic may be amorphous or in the crystalline state. Such formulations may also contain a buffering agent, solubilizing agent, clarifying agent, stabilizing agent, or other excipient. An example of a pharmaceutical composition of this invention for i.v. use comprises 500 mg. of the dry powder of the antibiotic or a pharmaceutically acceptable salt thereof in a 10 ml. sterile rubber-stoppered ampoule. Another such composition comprises 4 g. of dry powder of the antibiotic in a 100 ml. sterile ampoule. A further composition comprises 10 g. of the antibiotic as a dry powder in a sealed, sterile plastic pouch.

This invention also provides a method for treating bacterial infections in a mammal (man and animals) which comprises administering in an effective dose of between about 100 mg. and about 2 g. of an antibiotic compound of claim 1 or a pharmaceutically acceptable non-toxic salt thereof.

In practicing the method of this invention, the antibiotic can be administered i.v., i.m. or s.c. The antibiotic may be administered in a single dose or in multiple doses, for example, one to four times daily. Administration of the dose by i.v. infusion can be carried out over an extended time interval, for example, with hospitalized patients over one to two hours. The method may also be practiced by administering the dose simultaneously with an i.v. fluid such as plasma, a plasma extender, 5% dextrose, or glucose, by the piggy-back procedure. Commonly for i.v. infusion a unit dosage composition of the antibiotic in a plastic i.v. pouch is dissolved in the desired volume of diluent and the solution is infused.

A preferred treatment method of this invention comprises administering a preferred antibiotic of the invention as defined hereinabove.

The invention is further illustrated by the following examples wherein the abbreviations used have the following meanings.

TMSI is trimethylsilyliodide; THF is tetrahydrofuran; HPLC is high performance liquid chromatography; NMR is nuclear magnetic resonance spectrum; DMSOd₆ is deuterated dimethylsulfoxide; and the letters characterizing the NMR signals are as follows: s is singlet, d is doublet, q is quartet, m is multiplet, v is very, and b is broad.

The NMR spectra were run on a JEOL FX-90.

EXAMPLE 1 syn-7-[2-(2-Aminothiazol-4-yl)-2-methoxyiminoacetamido]-3-(thieno[2,3-b]pyridinium-7-ylmethyl)-3-cephem-4-carboxylate.

To a suspension of 910 mg. of syn-7-[2-(2-aminothiazol-4-yl)-2-methoxyiminoacetamido]-3-acetoxymethyl-3-cephem-4-carboxylic acid in 4 ml. of chloroform were added 1.25 ml. of N-methyl-N-trimethylsilyltrifluoroacetamide, and the suspension was stirred for one hour when a solution of the silylated derivative was obtained. To the solution were added by pipette 800 μl. of TMSI and the reaction mixture was stirred for 15 minutes and was then evaporated. The residue of the silylated 3-iodomethyl derivative was dissolved in 4 ml. of acetonitrile and 175 μl. of THF were added to the solution by means of a syringe. The solution was stirred for 5 minutes after which a solution of 324 mg. of thieno[2,3-b]pyridine in 1 ml. of acetonitrile was added to the solution. The reaction mixture was stirred for 3 hours at room temperature and was then treated with 135 μl. of water. The product, 850 mg., was separated by filtration and was purified by reverse phase C₁₈ silica HPLC using acetonitrile-acetic acid-water, 5-2-93 percent by volume. There were obtained 125 mg. of the product as purified.

NMR (DMSOd₆): signals at 9.6 (m, 2H), 9.05 (m, 1H), 8.31 (d, 1H), ca 8.2 (m, 1H), 7.89 (bs, 2H), 6.72 (s, 1H), ca 5.7 (bm, 3H), 5.08 (d, 1H), 3.79 (s, 3H), and ca 3.5 (m, 2H+water protons) delta.

EXAMPLE 2 syn-7-[2-(2-Aminothiazol-4-yl)-2-methoxyiminoacetamido]-3-(thieno[3,2-b]pyridinium-4-ylmethyl)-3-cephem-4-carboxylate.

The title compound was prepared by reacting syn-7-[2-(2-aminothiazol-4-yl)-2-methoxyiminoacetamido]-3-iodomethyl-3-cephem-4-carboxylic acid trimethylsilyl ester with thieno[3,2-b]pyridine by following the procedures described by Example 1.

NMR (DMSOd$_6$): signals at 3.2 (q, 2H, C$_2$-H$_2$), 3.8 (s, 3H, OCH$_3$), 5.0 (d, 1H, C$_6$-H), 5.6 (q, 1H, C$_7$-H), 5.8 (q, 2H, C$_{3'}$-H), 6.65 (s, 1H, thiazole H), 7.2 (s, 2H, NH$_2$), 7.2–9.6 (multi signals for thienopyridine), and 9.6 (d, 1H, NH) delta.

EXAMPLE 3 syn-7-[2-(5-Amino-1,2,4-thiadiazol-3-yl)-2-methoxyiminoacetamido]-3-(thieno[2,3-c]pyridinium-6-ylmethyl)-3-cephem-4-carboxylate.

The title compound is prepared by reacting syn-7-[2-(5-amino-1,2,4-thiadiazol-3-yl)-2-methoxyiminoacetamido]-3-iodomethyl-3-cephem-4-carboxylic acid trimethylsilyl ester with thieno[2,3-c]pyridine.

EXAMPLE 4 syn-7-[2-(Pyrazol-5-yl)-2-ethoxycarbonylmethoxyiminoacetamido]-3-(thieno[2,3-c]pyridinium-6-ylmethyl)-3-cephem-4-carboxylate is prepared with thieno[2,3-c]pyridine and syn-7-[2-(pyrazol-5-yl)-2-ethoxycarbonylmethoxyiminoacetamido]-3-iodomethyl-3-cephem-4-carboxylic acid trimethylsilyl ester.

EXAMPLE 5 syn-7-[2-(2-Aminopyrimidin-5-yl)-2-ethoxyiminoacetamido]-3-(thieno[3,2-c]pyridinium-5-ylmethyl)-3-cephem-4-carboxylate is prepared with thieno[3,2-c]pyridine and syn-7-[2-(2-aminopyrimidin-5-yl)-2-ethoxyiminoacetamido]-3-iodomethyl-3-cephem-4-carboxylic acid trimethylsilyl ester.

EXAMPLE 6 syn-7-[2-(2-Aminopyridin-6-yl)-2-methoxyiminoacetamido]-3-(thieno[2,3-b]pyridinium-7-ylmethyl)-3-cephem-4-carboxylate is prepared with thieno[2,3-b]pyridine and syn-7-[2-(2-aminopyridin-6-yl)-2-methoxyiminoacetamido]-3-iodomethyl-3-cephem-4-carboxylic acid trimethylsilyl ester.

EXAMPLE 7 syn-7-[2-(2-Aminothiazol-4-yl)-2-methoxyiminoacetamido]-3-(thieno[2,3-c]pyridinium-6-ylmethyl-3-cephem-4-carboxylate was prepared with trimethylsilylated syn-7-[2-(2-aminothiazol-4-yl)-2-methoxyiminoacetamido]-3-iodomethyl-3-cephem-4-carboxylic acid and thieno[2,3-c]pyridine by the procedure of Example 1.

NMR (DMSOd$_6$): signals at ca 3.2 (q, 2H, C$_2$-H$_2$, masked by HOD), 3.8 (s, 3H, OCH$_3$), 5.05 (d, 1H, C$_6$-H), 5.2 (s), 5.6 (q, 1H, C$_7$-H), 5.9 (s), 6.7 (s, 1H, thiazole-H), 7.2 (s, 2H, NH$_2$), and 7.95, d; 8.55, d; 9.45, m; 10.45, (s, thienopyridinium H) delta.

EXAMPLE 8 syn-7-[2-(2-Aminothiazol-4-yl)-2-methoxyiminoacetamido]-3-(thieno[3,2-c]pyridinium-5-ylmethyl)-3-cephem-4-carboxylate was prepared by reacting trimethylsilylated syn-7-[2-(2-aminothiazol-4-yl)-2-methoxyiminoacetamido]-3-iodomethyl-3-cephem-4-carboxylic acid with thieno[3,2-c]pyridine by following the procedures described by Example 1.

NMR (DMSOd$_6$): signals at 3.3 (q, 2H, C$_2$-H), 3.8 (s, 3H, OCH$_3$), 5.1 (d, 1H, C$_6$-H), 5.7 (m, 2H, C$_{3'}$-H), 6.7 (s, 1H, thiazole-H), 7.2 (s, 2H, NH$_2$), and 8.0–10.0 (thienopyridinium H) delta.

UV: $\lambda$max 255; $\epsilon = 19,557$.

EXAMPLE 9 syn-7-[2-(2-Aminopyridin-6-yl)-2-methoxyiminoacetamido]-3-(thieno[2,3-c]pyridinium-6-ylmethyl)-3-cephem-4-carboxylate is prepared by first silylating syn-7-[2-(2-aminopyridin-6-yl)-2-methoxyiminoacetamido]-3-acetoxymethyl-3-cephem-4-carboxylic acid with N-methyl-N-trimethylsilyltrifluoroacetamide. The silylated derivative is reacted with trimethylsilyliodide to prepare the corresponding silylated 3-iodomethyl derivative and the latter is reacted with thieno[2,3-c]pyridine to provide the pyridinium product.

EXAMPLE 10 syn-7-[2-(2-Aminopyridin-6-yl)-2-methoxyiminoacetamido]-3-(thieno[3,2-c]pyridinium-5-ylmethyl)-3-cephem-4-carboxylate is prepared with syn-7-[2-(2-aminopyridin-6-yl)-2-methoxyiminoacetamido]-3-acetoxymethyl-3-cephem-4-carboxylic acid and thieno[3,2-c]pyridine by the silylation, iodination, and substitution reaction procedures described by Example 1.

EXAMPLE 11 syn-7-[2-(2-Aminothiazol-4-yl)-2-(2-carboxyprop-2-yl)oxyiminoacetamido]-3-(thieno[2,3-c]pyridinium-6-ylmethyl)-3-cephem-4-carboxylate is prepared by first silylating syn-7-[2-(2-aminothiazol-4-yl)-2-(2-carboxyprop-2-yl)oxyiminoacetamido]-3-acetoxymethyl-3-cephem-4-carboxylic acid with N-methyl-N-trimethylsilyltrifluoroacetamide and the silylated derivative is then iodinated with TMSI to the silylated 3-iodomethyl derivative. The latter is reacted with thieno[2,3-c]pyridine to provide the product.

EXAMPLE 12 syn-7-[2-(2-Aminothiazol-4-yl)-2-(2-carboxyprop-2-yl)oxyiminoacetamido]-3-(thieno[3,2-c]pyridinium-5-ylmethyl)-3-cephem-4-carboxylate was prepared with thieno[3,2-c]pyridine and the starting material used in Example 11 by following the procedures described by Example 1.

NMR (DMSOd$_6$): signals at 9.98 (s, 1H), 9.45 (d, 1H), 9.25 (d, 1H), 8.8 (d, 1H), 8.35 (d, 1H), 7.95 (d, 1H), 7.25 (s, 1H), 6.7 (s, 1H), 5.7 (q, 1H), 5.5 (q, 2H), 5.1 (d, 1H), 3.4 (q, 2H), 1.4 (s, 6H) delta.

UV: $\lambda$max. 238 n.m.; $\epsilon = 25,726$.

EXAMPLE 13 syn-7-[2-(2-Aminothiazol-4-yl)-2-methoxyiminoacetamido]-3-(thieno[3,4-b]pyridinium-4-ylmethyl)-3-cephem-4-carboxylate is prepared with the starting material employed in Example 1 and thieno[3,4-b]pyridine by employing the reagents, reaction conditions and procedures described by Example 1.

EXAMPLE 14 syn-7-[2-(2-Aminothiazol-4-yl)-2-methoxyiminoacetamido]-3-(furo[3,2-c]pyridinium-5-ylmethyl)-3-cephem-4-carboxylate.

A. Preparation of furo[3,2-c]pyridine

To a partial solution of 117.3 g. (0.85 mole) of furan-2-acrylic acid in one-liter of sieve dried acetone was added with stirring under nitrogen triethylamine (101 g.) and the solution was cooled in an ice-alcohol bath. To the cold solution were added over about 20 minutes 119.35 g. (1.1 mole) of ethyl chloroformate. The rate of addition was such to maintain the temperature of the solution below 30° C. After the solution was stirred for about 15 minutes, a solution of 74.5 g (1.3 mole) of sodium azide in 300 ml. of water was added at such a rate to maintain the temperature of the reaction mixture below about 10° C. The reaction mixture was stirred for one hour without external cooling and was poured onto 4 liters of crushed ice and the mixture stirred vigorously. The product was filtered, washed with ice water and vacuum dried to yield 131 g. of furan-2-acrylic acid azide.

A mixture of 150 ml. of diphenylmethane and 27 g. (145 mmole) of tributylamine was heated under nitrogen and reflux at 230° C. by means of a Wood's metal bath. To the hot mixture were added carefully and portionwise 25 g. of the azide prepared as described above. The temperature of the reaction mixture was held at about 225° C. to about 235° C. during the addition and thereafter at 245° C. for 30 minutes. The diphenylmethane was distilled from the reaction mixture under vacuum, the residue cooled and diluted with diethyl ether. The solid product was separated by filtration and recrystallized from hot water. The dried product, furopyridone of the formula

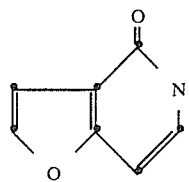

weighed 3.14 g. after drying.

The above 3.14 g. of the furopyridone was heated at the reflux temperature under nitrogen with stirring with 10 ml. of phosphorus oxychloride. Reflux was continued for 1.5 hours and the reaction mixture was then poured over ice. After the ice melted the product, 4-chlorofuro[3,2-c]pyridine, was extracted with diethyl ether. The extract was dried over sodium sulfate, filtered to remove drying agent, and evaporated to dryness to yield 3 g. of the product.

The 3 g. sample of the chlorofuropyridine was added to 35 ml. of glacial acetic acid and 7.5 g. of zinc metal were added to the solution. The reaction mixture was refluxed under nitrogen for 4 hours. After the reaction was complete, the mixture was filtered and the filtrate containing the furo[3,2-c]pyridine product was evaporated to dryness to yield 5.1 g. of crude product. The product was purified by chromatography on a column packed with silica in methylene chloride. The column was eluted sequentially with 500 ml. of methylene chloride, 500 ml. of 2% acetone in methylene chloride, 500 ml. of 4% acetone in methylene chloride, one liter of 8% acetone in methylene chloride, 500 ml. of 12% acetone in methylene chloride, and finally with acetone. The fractions containing the product as shown by TLC were combined and evaporated. The semi-solid product was dissolved in 30 ml. of methylene chloride and 30 ml. of water were added. The pH of the mixture was adjusted to 8.4 with 1N sodium hydroxide and the organic layer separated. The organic layer was dried over sodium sulfate, filtered and evaporated to dryness to yield 1.43 g. of furo[3,2-c]pyridine.

B. Preparation of Title Compound

A suspension of 910 mg. (2 mmole) of syn-7-[2-(2-aminothiazol-4-yl)-2-methoxyiminoacetamido]-3-acetoxymethyl-3-cephem-4-carboxylic acid in 5 ml. of methylene chloride was treated with 1.24 ml. (7 mmole) of N-methyl-N-trimethylsilyltrifluoroacetamide (MSTFA) and the mixture warmed to about 40° C. to achieve silylation. After the solution was formed, the solution was cooled to room temperature and 0.77 ml. (5.4 mmole) of TMSI was added by syringe. The reaction mixture was stirred at room temperature under nitrogen for ¾ hour and was then evaporated to a brown oil. The oil was dissolved in 5 ml. of acetonitrile and 0.73 ml. (9 mmole) of THF were added. The solution was stirred for 10 minutes. To this solution was added a solution of 286 mg. (2.4 mmole) of furo[3,2-c]pyridine in 5 ml. of acetonitrile to which had been added 0.43 ml. (2.4 mmole) MSTFA. The combined solutions were stirred at room temperature under nitrogen for 2 hours. The reaction mixture was diluted with diethyl ether and 3 drops of water were added to precipitate the product as a thick, tan solid. The mixture was sonicated, filtered, washed with diethyl ether, and dried at 40° C. for 1 hour under vacuum to yield 1.28 g. of the crude cephalosporin product. The product was purified via preparative HPLC using 5% acetonitrile, 2% acetic acid, and 93% water. There were obtained 14 mg. of the 2-cephem product and 580 mg. of the 3-cephem product as a white powder.

EXAMPLE 15 syn-7-[2-(2-Aminothiazol-4-yl)-2-methoxyiminoacetamido]-3-(furo[2,3-b]pyridinium-7-ylmethyl)-3-cephem-4-carboxylate was prepared by the reaction of the trimethylsilylated syn-7-[2-(2-aminothiazol-4-yl)-2-methoxyiminoacetamido]-3-iodomethyl-3-cephem-4-carboxylate with furo[2,3-b]pyridine.

NMR (DMSOd$_6$): signals at 9.4 (m, 2H), 8.1 (m, 2H), 7.2 (s, 2H), 6.7 (s, 1H), 5.65 (m, 3H), 5.05 (d, 1H), 3.8 (s, 3H), 3.2 (s, 2H) delta.

UV: λmax. 232 n.m.; ε=19,100. λmax. 252 n.m.; ε=18,000.

EXAMPLE 16 syn-7-[2-(2-Aminothiazol-4-yl)-2-(2-carboxyprop-2-yl)oxyiminoacetamido]-3-(5-ethylfuro[2,3-b]pryidinium-7-ylmethyl)-3-cephem-4-carboxylate is prepared by the reaction of trimethylsilylated syn-7-[2-(2-aminothiazol-4-yl)-2-(2-carboxyprop-2-yl)oxyiminoacetamido]-3-iodomethyl-3-cephem-4-carboxylate with 5-ethylfuro[2,3-b]pyridine.

EXAMPLE 17 syn-7-[2-(2-Aminothiazol-4-yl)-2-isopropoxyiminoacetamido]-3-(2-methylfuro[3,2-b]pyridinium-4-ylmethyl)-3-cephem-4-carboxylate is prepared by the reaction of the trimethylsilyl derivative of syn-7-[2-(2-aminothiazol-4-yl)-2-isopropoxyiminoacetamido]-3- iodomethyl-3-cephem-4-carboxylate with 2-methylfuro[3,2-b]pyridine.

EXAMPLES 18–37

By following the general procedure described in the preceding Examples, the following compounds of the formula 1 are prepared with the corresponding silylated 3-iodomethyl derivative and the indicated bicyclicpyridine.

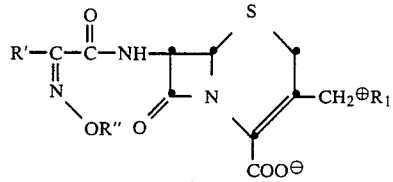

| Example No. | R' | R'' | ⊕R₁ |
|---|---|---|---|
| 18 | 2-aminothiazol-4-yl | H | thieno[3,2-c]pyridinium |
| 19 | " | H | furo[3,2-c]pyridinium |
| 20 | 5-aminoisothiazol-3-yl | CH₃ | " |
| 21 | 5-amino-1,2,4-thiadiazol-3-yl | C₂H₅ | " |
| 22 | " | —C(O)NHCH₃ | " |
| 23 | " | —C(CH₃)₂COOH | " |
| 24 | " | " | furo[2,3-b]pyridinium |
| 25 | pyrazol-5-yl | —CH₂COC₂H₅ | furo[3,2-b]pyridinium |
| 26 | " | " | furo[3,2-c]pyridinium |
| 27 | 3-aminopyrazol-5-yl | " | " |
| 28 | 2-aminopyridin-6-yl | CH₃ | " |
| 29 | " | " | furo(2,3-b]pyridinium |
| 30 | 2-aminopyrimidin-5-yl | —C(CH₃)₂COOH | " |
| 31 | " | " | furo[3,2-c]pyridinium |
| 32 | 5-amino-1,2,4-thiadiazol-3-yl | " | 2-methylfuro[3,2-c]pyridinium |
| 33 | 2-aminothiazol-4-yl | CH₃ | 2-methylfuro[2,3-c]pyridinium |
| 34 | " | " | 3-carboxyfuro[2,3-c]pyridinium |
| 35 | " | " | 4-carbamoylfuro[2,3-c]pyridinium |
| 36 | " | " | 3-chlorofuro[2,3-c]pyridinium |
| 37 | " | " | furo[2,3-c]pyridinium |

EXAMPLE 38 syn-7-[2-(2-Aminothiazol-4-yl)-2-methoxyiminoacetamido]-3-(2-methylfuro[3,2-b]pyridinium-4-ylmethyl)-3-cephem-4-carboxylate.

syn-7-[2-(2-Aminothiazol-4-yl)-2-methoxyiminoacetamido]-3-acetoxymethyl-3-cephem-4-carboxylic acid, 910 mg. (2 mmole) were suspended in 5 ml. of methylene chloride and the suspension treated with 1.24 ml. (7 mmole) of MSTFA under nitrogen. The suspension was heated at 40° C. until a solution of the silylated derivative was formed (5 minutes). The solution was cooled to room temperature and 0.77 ml. (5.4 mmole) of TMSI was added with a syringe. The solution was stirred for about 45 minutes at room temperature under nitrogen to form the silylated 3-iodomethyl derivative. Thereafter, a solution of 319 mg. (2.4 mmole) of 2-methylfuro[3,2-b]pyridine in 10 ml. of acetonitrile was added to the reaction solution and the mixture was stirred for about 3 hours. The reaction mixture was then diluted with diethyl ether and two drops of water were added. The thick tan precipitate which formed was sonicated, filtered, washed with diethyl ether and dried under vacuum at 40° C. to give 1.03 g. of the crude product. The product was purified over C₁₈ silica gel reverse phase chromatography using 5% acetonitrile:2% acetic acid:93% water, v:v:v to give 348 mg. of the purified product.

NMR (90 MHz, DMSOd₆) δ 9.45 (d, 1H), 9.3 (d, 1H), 8.7 (d, 1H), 7.9 (m, 1H), 7.75 (s, 1H), 7.15 (s, 2H), 6.65 (s, 1H), 5.6 (m, 3H), 5.0 (d, 1H), 3.8 (s, 3H), 3.4 (q, 2H), 2.7 (s, 3H).

UV: λmax 256 n.m.; ε=17,924.

EXAMPLE 39 syn-7-[2-(2-Aminothiazol-4-yl)-2-methoxyiminoacetamido]-3-(2-methylfuro[2,3-c]pyridinium-6-ylmethyl)-3-cephem-4-carboxylate.

By following the procedures and conditions of the preceding Example 38, 910 mg. (2 mmole) of the same starting material was converted to the silylated 3-iodomethyl derivative and the latter reacted with 2-methylfuro[2,3-c]pyridine. The product was precipitated, recovered and purified by procedures described in Example 38 to give 526 mg. of the purified title compound.

NMR (90 MHz, DMSOd₆) δ 10.03 (s, 1H), 9.45 (d, 1H), 9.15 (d, 1H), 8.15 (d, 1H), 7.1 (s, 3H), 6.65 (s, 1H), 5.6 (m, 2H), 5.05 (m, 2H), 3.75 (s, 3H), 3.3 (q, 2H), 2.65 (s, 3H).

UV: λmax 268 n.m.; ε=22,278.

EXAMPLE 40 syn-7-[2-(2-Aminothiazol-4-yl)-2-methoxyiminoacetamido]-3-(2-carboxythieno[3,2-c]pyridinium-5-ylmethyl)-3-cephem-4-carboxylate.

A. 2-Carboxythieno[3,2-c]pyridine

Freshly distilled diisopropylamine (18.15 g., 180 mMole) was dissolved in sieve-dried tetrahydrofuran (200 ml.). The solution was cooled to −20° C., and stirred under a nitrogen blanket. n-Butyl lithium (176 mM) was then added, with care being taken to ensure that the temperature did not rise above −20° C. The temperature of the reaction mixture was then dropped to −70° C. using dry ice/acetone. A solution of thieno[3,2-c]pyridine (150 mMole) in tetrahydrofuran was added dropwise taking care to ensure that the temperature did not rise above −65° C. The addition was complete after 20 minutes during which period stirring was continued. Carbon dioxide gas was then bubbled into the reaction mixture in such a way that the temperature remained below −60° C. for 30 minutes, −40° C. for 1 hour and, finally, under −15° C. for 30 minutes. Solvent was evaporated off in vacuo, and the residue was dissolved in water. The aqueous diisopropylammonium salt of the title compound was washed (×3) with methylene chloride, and 120 ml. of 5N sodium hydroxide was then added. Cooling in ice water with stirring resulted in the precipitation of the sodium salt (24.8 g., after filtration under vacuum and drying).

This sodium salt was then dissolved in 10% aqueous methanol and the solution acidified to pH 6.0 with concentrated hydrochloric acid. After filtration and drying under vacuum there was obtained 19 g. of the title product.

NMR (DMSOd$_6$): signals at 8.1 (d, 1 proton), 8.2 (s, 1 proton), 8.5 (d, 1 proton), 9.1 (s, 1 (proton).

A solution of the 2-carboxythieno[3,2-c]pyridine in acetonitrile was treated with MSTFA and the solution of the trimethylsilyl derivative was added to a solution of the 3-iodomethyl silylated cephalosporin to provide the title compound.

NMR (DMSOd$_6$): signals at 9.7 (s, 1H), 9.5 (d, 1H), 9.0 (d, 1H), 8.7 (d, 1H), 8.1 (s, 1H), 7.1 (s, 2H), 6.7 (s, 1H), 5.7 (q, 1H), 5.3 (d, 2H), 5.1 (d, 1H), 3.8 (s, 3H), 3.4 (q, 2H) delta.

UV: λmax. 245 n.m.; ε=46,000.

The compounds of the following Examples 41–48 were prepared with the substituted or unsubstituted thieno or furopyridine by the procedures described in the foregoing Examples.

EXAMPLE 41 syn-7-[2-(2-Aminothiazol-4-yl)-2-methoxyiminoacetamido]-3-(2-methylthieno[3,2-c]pyridinium-5-ylmethyl)-3-cephem-4-carboxylate.

NMR (DMSOd$_6$): signals at 9.8 (s, 1H), 9.5 (d, 1H), 9.2 (d, 1H), 8.65 (d, 1H), 7.6 (s, 1H), 7.15 (s, 2H), 6.7 (s, 1H), 5.45 (m, 3H), 5.05 (d, 1H), 3.8 (s, 3H), 3.3 (q, 2H), 2.7 (s, 3H) delta.

UV: λmax. 242 n.m.; ε=31,614.

EXAMPLE 42 syn-7-[2-(2-Aminothiazol-4-yl)-2-methoxyiminoacetamido]-3-(3-bromothieno[3,2-c]pyridinium-5-ylmethyl)-3-cephem-4-carboxylate.

NMR (DMSOd$_6$): signals at 10.04 (s, 1H), 9.45 (m, 2H), 8.8 (d, 1H), 8.5 (s, 1H), 7.15 (s, 2H), 6.65 (s, 1H), 5.6 (q, 1H), 5.5 (q, 2H), 5.05 (d, 1H), 3.75 (s, 3H), 3.3 (q, 2H) delta UV: λmax. 244 n.m.; ε=33,500.

EXAMPLE 43 syn-7-[2-(Aminothiazol-4-yl)-2-methoxyiminoacetamido]-3-(2-methoxycarbonylthieno[3,2-c]pyridinium-5-ylmethyl)-3-cephem-4-carboxylate.

NMR (DMSOd$_6$): signals at 10.1 (s, 1H), 9.45 (m, 2H), 8.8 (d, 1H), 8.55 (s, 1H), 7.15 (s, 2H), 6.65 (s, 1H), 5.6 (q, 1H), 5.45 (q, 2H), 5.05 (d, 1H), 3.95 (s, 3H), 3.8 (s, 3H), 3.3 (q, 2H) delta.

UV: λmax. 243 n.m.; ε=52,500.

EXAMPLE 44 syn-7-[2-(2-Aminothiazol-4-yl)-2-methoxyiminoacetamido]-3-(furo[3,2-b]pyridinium-4-ylmethyl)-3-cephem-4-carboxylate.

NMR (DMSOd$_6$): signals at 9.4 (m, 2H), 8.85 (m, 2H), 8.0 (m, 2H), 7.15 (s, 2H), 6.65 (s, 1H), 5.6 (m, 3H), 4.95 (d, 1H), 3.7 (s, 3H), 3.15 (q, 2H) delta.

UV: λmax. 260 n.m.; ε=22,844.

EXAMPLE 45 syn-7-[2-(2-Aminothiazol-4-yl)-2-methoxyiminoacetamido]-3-(furo[2,3-c]pyridinium-6-ylmethyl)-3-cephem-4-carboxylate.

NMR (DMSOd$_6$): signals at 10.2 (s, 1H), 9.5 (d, 1H), 9.3 (d, 1H), 8.8 (s, 1H), 8.35 (d, 1H), 7.45 (s, 1H), 7.15 (s, 2H), 6.65 (s, 1H), 5.65 (q, 1H), 5.4 (q, 2H), 5.05 (d, 1H), 3.75 (s, 3H), 3.3 (q, 2H) delta.

UV: λmax. 263 n.m.; ε=20,642.

EXAMPLE 46 syn-7-[2-(2-Aminothiazol-4-yl)-2-methoxyiminoacetamido]-3-(3-carboxythieno[3,2-c]pyridinium-5-ylmethyl)-3-cephem-4-carboxylate NMR (DMSOd$_6$): signals at 10.2 (s, 1H), 9.5 (d, 1H), 9.3 (d, 1H), 8.9 (m, 2H), 7.2 (s, 2H), 6.7 (s, 1H), 5.7 (m, 1H), 5.5 (m, 2H), 5.1 (d, 1H), 3.8 (s, 3H), and 3.4 (q, 2H) delta.

EXAMPLE 47 syn-7-[2-(2-Aminothiazol-4-yl)-2-methoxyiminoacetamido]-3-(2-aminothieno[3,2-c]pyridinium-5-ylmethyl)-3-cephem-4-carboxylate NMR (DMSOd$_6$): signals at 9.5 (d, 1H), 9.2 (s, 1H), 8.7 (d, 1H), 8.3 (d, 2H), 7.3 (s, 2H), 7.2 (s, 2H), 6.7 (s, 1H), 5.6 (m, 1H), 5.4 (m, 2H), 5.1 (d, 1H), 3.8 (s, 3H), and 3.3 (q, 2H) delta.

EXAMPLE 48 syn-7-[2-(2-Aminothiazol-4-yl)-2-methoxyiminoacetamido]-3-(2-formylthieno[3,2-c]pyridinium-5-ylmethyl)-3-cephem-4-carboxylate NMR (DMSOd$_6$): signals at 10.2 (d, 2H), 9.4 (m, 2H), 8.9 (d, 1H), 8.5 (s, 1H), 7.1 (s, 2H), 6.7 (s, 1H), 5.7 (m, 1H), 5.5 (m, 2H), 5.1 (d, 1H), 3.8 (s, 3H), and 3.2 (m, 2H) delta.

EXAMPLE 49 syn-7-[2-(2-Aminothiazol-4-yl)-2-methoxyiminoacetamido]-3-(thieno[3,2-c]pyridinium-5-ylmethyl)-3-cephem-4-carboxylate 7-Aminocephalosporanic acid (2.7 g, 10 mMole) and thieno[3,2-c]pyridine (3.0 g, 10 mMole) in the form of its tosylate salt was suspended in a mixture of water (25 ml) and acetonitrile (25 ml). The pH was adjusted to 7.3 with NaOH. The reaction mixture was then heated in an oil bath at 70° C. for 2¾ hours and then cooled to 0° C. at which time the pH was 6.8. The pH of the reaction mixture, was adjusted to 7.5 with further 2N NaOH. The product of the above procedure was:

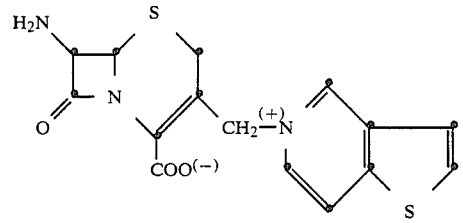

However, this product was not isolated but was used in situ in the next step in the reaction. In other words, the 7-amino nucleus depicted above was immediately acylated by adding the active ester syn-1-[(2-amino-4-thiazolyl)(methoxyimino)acetyl]-3-hydroxy-1H-benzotriazolium, hydroxide, inner salt (3.0 g.) in solid form to the reaction mixture. After ½ hour, the pH was adjusted to 7.3 with 2N NaOH and the reaction mixture allowed to stand for 16 hours. After standard work-up there was obtained 900 mg. of the title product.

NMR (DMSOd$_6$): signals at 3.3 (q, 2H), 3.8 (s, 3H), 5.1 (d, 1H), 5.7 (m, 2H), 6.7 (s, 1H), 7.2 (s, 2H), and 8-10 (thienopyridinium H) delta.

UV: λmax. 255 n.m.; ε=19,557.

We claim:

1. The compound of the formula

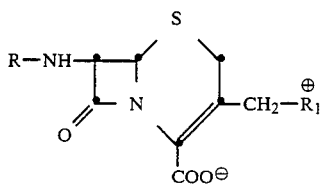

wherein R is hydrogen, formyl, aminoadipoyl, or protected aminoadipoyl; ⊕R$_1$ is a bicyclicpyridinium group selected from the group consisting of a thienopyridinium group of the formulas

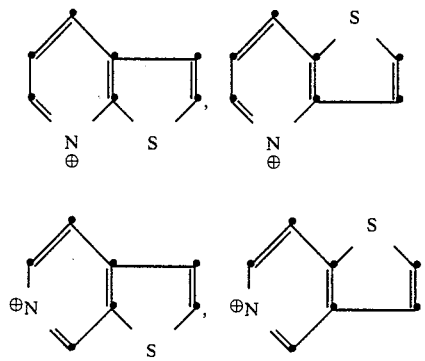

or a furopyridinium group of the formulas

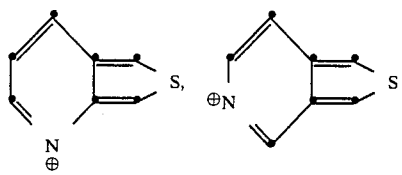

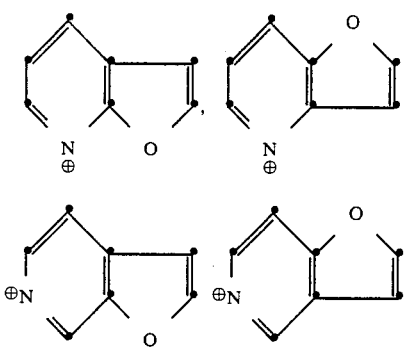

and said thienopyridinium and said furopyridinium wherein either or both of the hetero rings thereof is substituted by one or two C$_1$-C$_4$ alkyl, halogen, carboxy, carbamoyl, or C$_1$-C$_4$ alkoxycarbonyl groups.

2. The compound of claim 1 wherein ⊕R$_1$ is an unsubstituted or substituted thieno[2,3-b]pyridinium-7-yl, thieno[3,2-b]pyridinium-4-yl, thieno[2,3-c]pyridinium-6-yl, or thieno[3,2-c]pyridinium-5-yl group.

3. The compound of claim 1 wherein ⊕R$_1$ is a substituted or unsubstituted furopyridinium group.

4. The compound of claim 2 wherein R is hydrogen.

5. The compound of claim 3 wherein R is hydrogen.

6. The compound of claim 1 wherein R is protected aminoadipoyl.

7. The compound of claim 6 of the formula

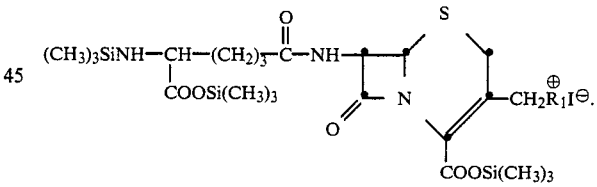

* * * * *